United States Patent
Scivoletto et al.

(10) Patent No.: US 6,429,218 B1
(45) Date of Patent: Aug. 6, 2002

(54) METHOD OF CONTROLLING NIACIN CONCENTRATION IN LOTION

(76) Inventors: Joseph Scivoletto, 10249 E. Paraiso Pl.; RoseMarie Scivoletto, 10249 El Paraiso Pl., both of Delray Beach, FL (US) 33446

( * ) Notice: Subject to any disclaimer, the term of this patent is extended or adjusted under 35 U.S.C. 154(b) by 0 days.

(21) Appl. No.: 09/711,376

(22) Filed: Nov. 14, 2000

Related U.S. Application Data

(63) Continuation-in-part of application No. 09/414,849, filed on Oct. 12, 1999, now Pat. No. 6,248,763.
(60) Provisional application No. 60/047,032, filed on May 19, 1997.

(51) Int. Cl.⁷ ............................................... A61K 31/44
(52) U.S. Cl. ...................................................... 514/356
(58) Field of Search ......................................... 514/356

(56) References Cited

U.S. PATENT DOCUMENTS

| | | | |
|---|---|---|---|
| 3,729,568 A | 4/1973 | Kligman et al. | 424/318 |
| 3,880,996 A | 4/1975 | Fisher | 424/184 |
| 3,906,108 A | 9/1975 | Felty | 424/318 |
| 3,912,666 A | 10/1975 | Spitzer et al. | 260/1.5 E |
| 4,505,896 A | 3/1985 | Bernstein | 424/164 |
| 4,968,685 A | 11/1990 | Grollier | 514/256 |
| 5,157,036 A | 10/1992 | Grollier | 514/256 |
| 5,240,945 A | 8/1993 | Warshaw | 514/356 |
| 5,468,492 A | 11/1995 | Szaloki et al. | 424/195.1 |
| 5,833,998 A | 11/1998 | Biedermann et al. | 424/401 |

FOREIGN PATENT DOCUMENTS

GB  2210789  6/1989

OTHER PUBLICATIONS

Fed. Register (1991), 56(159), 41008–20, Aug. 16, 1991 abstract.
IL 56964A1 abstract, 1982.

*Primary Examiner*—Rebecca Cook
(74) *Attorney, Agent, or Firm*—Oltman, Flynn & Kubler

(57) ABSTRACT

A method of controlling niacin (nicotinic acid), its esters and amides concentration in a lotion or cream by adding a niacin (nicotinic acid), its esters and/or amides based additive to a niacin (nicotinic acid), its esters and/or amides based base cream, serum or lotion.

3 Claims, No Drawings

METHOD OF CONTROLLING NIACIN CONCENTRATION IN LOTION

RELATED APPLICATIONS

This application is a continuation-in-part of application Ser. No. 09/414,849 filed on Oct. 12, 1999 now U.S. Pat. No. 6,248,763 by RoseMarie Scivoletto. Other related applications are Ser. No. 09/082,292 filed May 19, 1998 abandoned and Provisional Application No. 60/047,032 filed May 19, 1997.

FIELD OF THE INVENTION

The present invention relates to a method of controlling niacin (nicotinic acid) concentration in a skin lotion, and more particularly to a method which involves the addition of niacin (nicotinic acid) to a facial lotion, cream or serum after it is sold, for increasing the concentration of niacin (nicotinic acid) until the user exhibits a satisfactory degree of warmth, blush, flushing or redness, which may last from 15 to 30 minutes.

BACKGROUND OF THE INVENTION

Various niacin (nicotinic acid) based compositions have been proposed in co-pending patent application, Ser. No. 09/414,849 filed Oct. 12, 1999, which is incorporated herein by reference, for use as facial creams and facial lotions. A wide variety of compositions are possible. The most difficult problem with formulas that are formulated with nicotinic acid (niacin) and its amides and esters is finding the correct amounts of each of the active ingredients that are comfortable, effective and safe for the user. Because of the varying skin types, too little of the active ingredients can be ineffective, while too much can cause excessive warmth, pinching or tingling, extreme redness and plumping due to the increased vasodilation of the skin.

SUMMARY OF THE INVENTION

Applicant proposes to formulate nicotinic acid (niacin), amide or ester in a lotion, cream or serum with a desired percentage of niacin (nicotinic acid) and also package small ampoules containing niacin (nicotinic acid) so that when one ampoule or drops of the niacin (nicotinic acid) based formulation is added to the base ampoules by the user, niacin (nicotinic acid) concentration will be increased.

If one of the formulas from the aforesaid co-pending application is applied to the skin, it desirably has one of three strengths: sensitive, non-sensitive, or extra strength. If the user analyzes his or her skin type incorrectly, they can use a product that is too weak or too strong causing no reaction or too much reaction for a starting point. Many users, after using any of the formulas for a few weeks or months, want to up the strength for more desirable results.

The present invention overcomes this problem by providing a method of increasing the niacin (nicotinic acid) concentration in a lotion or cream, by adding niacin (nicotinic acid) to the base niacin (nicotinic acid) product after it is sold, thus increasing its strength for improved results and benefits. Accordingly, it is an object of the invention to provide a new method of increasing niacin (nicotinic acid) concentration in a cream or lotion for the skin after the product has been sold.

Another object of the invention is to provide effective formulations for the additive dose so that the user can achieve the desired degree of warmth, blush, flushing or redness of the skin.

A further object of the invention is to add the additional active ingredient dose by dose so that the user can control the niacin (nicotinic acid) concentrate to derive the most benefits for individual skin types and comfort levels.

Before explaining the disclosed embodiment of the present invention in detail it is to be understood that the invention is not limited in its application to the details of the particular arrangement shown, since the invention is capable of other embodiments. Also, the terminology used herein is for the purpose of description and not of limitation.

DETAILED DESCRIPTION

Applicant has found that skin flushing and reddening adds to the effect of reducing enlarged pores, minimizing fine lines, penetration of moisturizer ingredients, shrinking of pimples, removal of blackheads and other unwanted dirt or oxidents under the skin, tightening of the skin due to the flushing and topical circulation of the reddening. Applicant has found through experience and testing that even 0.06% of niacin (nicotinic acid) or its esters can cause reddening or flushing of the skin for people with sensitive skin and people who use glycolic acids or other peeling chemicals. For over-the-counter and mass marketing, it would be very difficult to analyze everyone's skin type to provide a cream or lotion which would produce a desirable degree of redness, blush or flushing.

Applicant proposes to allow consumers to add active ingredients to a skin lotion or cream as they use it and see the acceptable results. As their skin or condition improves, they can up the strength for further improved results and benefits until the desired results are achieved. The skin cream or lotion which is to be provided as the base product may be any one of the formulations disclosed in co-pending application, Ser. No. 09/414,849 filed Oct. 12, 1999. It could also be any one of the formulations described in the Proctor & Gamble patent U.S. Pat. No. 5,833,998. Furthermore, the following formulations are provided as examples of preferred embodiments.

| BODY HYDRATING CREAM (F335-RB6): | |
|---|---|
| Deionized Water | 35.0%–45.0% |
| Aloe Vera Gel | 35.0%–45.0% |
| Propylene Glycol (and) Methyl Paraben (and) Propyl Paraben (and) Diazolidinyl Urea | 0.5%–1.15% |
| Sodium Laurel Sulfate | 0.20%–1.20% |
| Triethanolamine | 0.50%–1.75% |
| Cetyl Alcohol | 2.00%–5.00% |
| Isopropyl Palmitate | 2.50%–5.50% |
| Isopropyl Myristate | 2.50%–5.50% |
| Jojoba Oil | 0.50%–3.00% |
| Tocopherol Acetate (Vit-E) | 0.03%–2.03% |
| Isosteryl Palmitate | 3.50%–7.50% |
| Methyl Nicotinate | 0.01%–1.5% |
| Niacin (nicotinic acid) | 0.01%–1.5% |
| Herbal Fragrance | 0.05%–0.35% |
| FACIAL CREAM (F335-RC-6): | |
| Deionized Water | 35.0%–45.0% |
| Aloe Vera Gel | 35.0%–45.0% |
| PEG-8 | 2.0%–5.5% |
| Propylene Glycol (and) Methyl Paraben (and) Propyl Paraben (and) Diazolidinyl Urea | 0.5%–1.15% |
| Sodium Laurel Sulfate | 0.20%–1.20% |
| Triethanolamine | 0.50%–1.75% |
| Cetyl Alcohol | 2.00%–5.00% |
| Isopropyl Palmitate | 2.50%–5.50% |

-continued

| | |
|---|---|
| Isopropyl Myristate | 2.50%–5.50% |
| Jojoba Oil | 0.50%–3.00% |
| Tocopherol Acetate (Vit-E) | 0.03%–2.03% |
| Isosteryl Palmitate | 3.50%–7.50% |
| Methyl Nicotinate | 0.01%–1.5% |
| Ascorbyl Palmitate (Vit-C) | 0.01%–1.5% |
| Niacin (nicotinic acid) | 0.01%–1.5% |
| Herbal Fragrance | 0.05%–0.35% |
| CELLULITE SERUM (1033-6): | |
| Deionized Water | 40.00%–50.00% |
| Aloe Vera Gel | 40.00%–60.00% |
| Isopropyl Myristate | 3.50%–7.50% |
| Polyacrylamide (and) C13–14 Isoparaffin (and) Laureth-7 | 1.50%–3.00% |
| Methyl Nicotinate | 0.01%–1.5% |
| Glycerine | 0.75%–3.25% |
| Niacin (nicotinic acid) | 0.01%–1.5% |
| Tetrasodium EDTA | 0.05%–1.25% |
| DMDM Hydantoin | 0.10%–0.50% |
| Fragrance | 0.05%–0.35% |
| Tocopherol Acetate (Vit-E) | 0.01%–1.01% |
| Hydrolyzed Silk Proteins | 0.01%–1.01% |
| Hydrolyzed Collagen | 0.01%–1.01% |
| FACE CREAM FOR EXTRA OILY SKIN | |
| Methyl Nicotinate | 0.01%–2.5% |
| Niacin (nicotinic acid) | 0.01%–2.5% |
| Aloe Vera gel | 35–45% |
| Glycerin | 0.8%–1.8% |
| DMDM Hydantoin | 0.02%–0.25% |
| Tetrasodium EDTA | 0.05%–0.15% |
| Vit-E | 0.01%–0.1% |
| Polysorbate-20 | 0.5%–1.0% |
| Silk Amino Acids | 0.01%–0.1% |
| Hydrolyzed Collagen | 0.01%–0.1% |

The latter formula can be used with moisturizer products or alone for extra oily facial skin. It is also preferred as the additive for increasing the strength of the base formula. Both the base formula and the additive may be sold at the same time. The added strength ampoule or small plastic bottle may be from ⅓ oz. and up, with 0.01% to 3% of nicotinic acid (niacin)and esters, and amides at 0.01% to 20% to be used with all formulas.

In one example, a 2 oz. bottle of lotion or cream with 0.06% niacin (nicotinic acid) as the active ingredient is sold along with one (1) or more ⅓ oz. or more ampoules with each ampoule at 0.4% niacin (nicotinic acid), so that the user can increase the strength of the active ingredient little by little to the desired level of warmth and blush. The niacin (nicotinic acid) strength at the time of adding one ampoule of the active ingredient will be 0.15% to 0.21%, and so on with each addition ampoule used.

In all formulas other active ingredients for other skin conditions such as acne and psoriasis may be used. Such active ingredients may be glycolic acid, resorcinol monacetate, salicylic acid and witch hazel. S.P.F. (Sun Protection Factor) 2% to 30% for longer lasting sun block or sun screen can also be added to the formulas.

I claim:

1. A method of reducing enlarged pores, minimizing fine lines, shrinking pimples, removing blackheads or tightening the skin which comprises applying to the areas of the skin in need of said method a lotion, serum or cream comprising:
   a base cream, serum or lotion having an effective concentration of niacin (nicotinic acid) or its esters or amides, for said method to which the niacin concentration has been further increased by the addition of niacin (nicotinic acid) in a cream, serum or lotion in a concentration effective to produce a desired degree of warmth, blush, flushing or reddening of the skin when applied to the skin.

2. The method of claim 1, wherein the concentration of niacin (nicotinic acid) in said cream, serum or lotion which is added comprises 0.1% to 3% by weight.

3. The method of claim 1, wherein additional amounts of said additive cream, serum or lotion are added to the base cream, serum or lotion on a dose by dose basis until the desired degree of warmth, blush, flushing or redness is obtained.

* * * * *